US010220111B2

(12) United States Patent
Röder et al.

(10) Patent No.: US 10,220,111 B2
(45) Date of Patent: Mar. 5, 2019

(54) HIGHLY ABSORBENT POLYSACCHARIDE FIBER AND USE THEREOF

(71) Applicant: LENZING AG, Lenzing (AT)

(72) Inventors: Thomas Röder, Vöcklabruck (AT); Gernot Kaindl, Lenzing (AT); Sigrid Redlinger, Lenzing (AT); Heinrich Firgo, Vöcklabruck (AT); Gert Kroner, Seewalchen (AT)

(73) Assignee: LENZING AKTIENGESELLSCHAFT, Lenzing (AT)

(*) Notice: Subject to any disclaimer, the term of this patent is extended or adjusted under 35 U.S.C. 154(b) by 302 days.

(21) Appl. No.: 14/899,214

(22) PCT Filed: Jun. 13, 2014

(86) PCT No.: PCT/AT2014/000125
§ 371 (c)(1),
(2) Date: Dec. 17, 2015

(87) PCT Pub. No.: WO2014/201484
PCT Pub. Date: Dec. 24, 2014

(65) Prior Publication Data
US 2016/0144065 A1 May 26, 2016

(30) Foreign Application Priority Data
Jun. 17, 2013 (AT) .................. A 483/2013

(51) Int. Cl.
| | | |
|---|---|---|
| A61L 15/28 | (2006.01) | |
| B01J 20/24 | (2006.01) | |
| C08B 37/00 | (2006.01) | |
| C08L 5/00 | (2006.01) | |
| D04H 1/28 | (2012.01) | |
| D04H 3/013 | (2012.01) | |
| D01F 2/06 | (2006.01) | |
| D01F 9/00 | (2006.01) | |
| D04H 1/4258 | (2012.01) | |
| C08L 1/02 | (2006.01) | |

(52) U.S. Cl.
CPC .............. *A61L 15/28* (2013.01); *B01J 20/24* (2013.01); *C08B 37/0009* (2013.01); *C08L 1/02* (2013.01); *C08L 5/00* (2013.01); *D01F 2/06* (2013.01); *D01F 9/00* (2013.01); *D04H 1/28* (2013.01); *D04H 1/4258* (2013.01); *D04H 3/013* (2013.01)

(58) Field of Classification Search
CPC .................. A61L 15/28; B01J 20/24
See application file for complete search history.

(56) References Cited

U.S. PATENT DOCUMENTS

| | | | |
|---|---|---|---|
| 2,179,181 | A | 11/1939 | Graenacher et al. |
| 2,914,414 | A | 11/1959 | Novak et al. |
| 3,447,939 | A | 6/1969 | Johnson |
| 3,600,379 | A | 8/1971 | Sihtola et al. |
| 3,844,287 | A | 10/1974 | Smith |
| 4,129,679 | A | 12/1978 | Woodings |
| 4,289,824 | A | 9/1981 | Smith |
| 4,306,059 | A | 12/1981 | Yokobayashi et al. |
| 4,562,020 | A | 12/1985 | Hijiya et al. |
| 5,403,530 | A | 4/1995 | Taylor |
| 5,589,125 | A | 12/1996 | Zikeli et al. |
| 5,725,821 | A | 3/1998 | Gannon et al. |
| 5,795,522 | A | 8/1998 | Firgo et al. |
| 6,042,769 | A | 3/2000 | Gannon et al. |
| 6,113,842 | A | 9/2000 | Weigel et al. |
| 6,284,479 | B1 | 9/2001 | Nichols |
| 6,821,591 | B2 | 11/2004 | Gord et al. |
| 7,000,000 | B1 | 2/2006 | O'Brien |
| 9,175,423 | B2 | 11/2015 | O'Brien et al. |
| 9,701,800 | B2 | 7/2017 | Durnberger et al. |
| 10,030,323 | B2 | 7/2018 | Durnberger et al. |
| 2002/0022100 | A1 | 2/2002 | Gord et al. |
| 2002/0167110 | A1 | 11/2002 | Schlossnikl et al. |
| 2003/0185863 | A1 | 10/2003 | Bengs et al. |
| 2009/0165969 | A1 | 7/2009 | Luo |
| 2011/0200776 | A1 | 8/2011 | Zikeli et al. |
| 2013/0087938 | A1 | 4/2013 | O'Brien et al. |
| 2013/0161562 | A1 | 6/2013 | O'Brien et al. |
| 2013/0161861 | A1 | 6/2013 | O'Brien et al. |
| 2013/0244288 | A1 | 9/2013 | O'Brien et al. |
| 2013/0313737 | A1 | 11/2013 | O'Brien |
| 2014/0367896 | A1 | 12/2014 | Zikeli et al. |
| 2016/0053061 | A1 | 2/2016 | Durnberger et al. |

(Continued)

FOREIGN PATENT DOCUMENTS

| | | |
|---|---|---|
| AT | 287.905 B | 2/1971 |
| AT | 287905 B | 2/1971 |

(Continued)

OTHER PUBLICATIONS

Akira Misaki, Elsinan, an Extracellular alpha 1,3:1,4 Glucan Produced by Elsinoe leucospila: Production, Structure, Properties and Potential Food Utilization, Foods Food Ingredients J. Jpn, vol. 209, No. 4, Jan. 1, 2004, available at: http://www.ffcr.or.jp/zaidan/ffcrhome.nsf/7bd44c20b0dc562649256502001b65e9/a574be4bca4c288149256e82000f39bb/$FILE/209(4)3.pdf.

(Continued)

*Primary Examiner* — Peter F Godenschwager
(74) *Attorney, Agent, or Firm* — Venable LLP

(57) ABSTRACT

The present invention relates to a method for the production of highly absorbent polysaccharide fibers which contain a mixture of cellulose and $\alpha(1\rightarrow 3)$-glucan as a fiber-forming substance, as well as to the highly absorbent fibers made thereby, and to their use.

20 Claims, No Drawings

(56) References Cited

U.S. PATENT DOCUMENTS

| | | | |
|---|---|---|---|
| 2016/0053406 A1 | 2/2016 | Durnberger et al. |
| 2016/0060792 A1 | 3/2016 | Durnberger et al. |
| 2016/0138195 A1 | 5/2016 | Kraft et al. |
| 2016/0138196 A1 | 5/2016 | Roder et al. |
| 2016/0177471 A1 | 6/2016 | Kraft et al. |
| 2017/0283568 A1 | 10/2017 | Durnberger et al. |

FOREIGN PATENT DOCUMENTS

| | | | |
|---|---|---|---|
| AT | 402828 B | 9/1997 |
| CA | 1082866 A | 8/1980 |
| DE | 2550345 A1 | 5/1977 |
| DE | 3036415 A1 | 4/1981 |
| DE | 19544097 C1 | 7/1997 |
| DE | 10029044 A1 | 1/2002 |
| DE | 10035798 A1 | 1/2002 |
| DE | 10261496 A1 | 7/2004 |
| EP | 0049710 A1 | 4/1982 |
| EP | 0 158 884 A2 | 10/1985 |
| EP | 0 328 317 A1 | 8/1989 |
| EP | 0 356 419 B1 | 12/1992 |
| EP | 0 584 318 B1 | 3/1994 |
| GB | 2062652 A | 5/1981 |
| JP | 0351366 H | 3/1991 |
| JP | 2006-211989 A | 8/2006 |
| WO | 89/01062 A1 | 2/1989 |
| WO | 95/35340 A1 | 12/1995 |
| WO | 97/04148 A1 | 2/1997 |
| WO | 97/07266 A1 | 2/1997 |
| WO | 98/42492 A2 | 10/1998 |
| WO | 98/55673 A1 | 12/1998 |
| WO | 00/23250 A1 | 4/2000 |
| WO | 00/43580 A1 | 7/2000 |
| WO | 2012/073019 A1 | 6/2012 |
| WO | 2013/006876 A1 | 1/2013 |
| WO | 2013020919 A1 | 2/2013 |
| WO | 2013/036918 A1 | 3/2013 |
| WO | 2013/036968 A1 | 3/2013 |
| WO | 2013030400 A1 | 3/2013 |
| WO | 2013/052730 A1 | 4/2013 |
| WO | 2014/099724 A1 | 6/2014 |
| WO | 2014/165881 A1 | 10/2014 |

OTHER PUBLICATIONS

Zhang, P. et al., Effects of urea and sodium hydroxide on the molecular weight and conformation of alpha-(1>3)-d-glucan from Lentinus edodes in aqueous solution, Carbohydrate Research, Pergamon, GB, Carbohydrate Research, Pergamon, GB, vol. 327 No. 4 pp. 431-438, Aug. 7, 2000.
Simpson, et al., *Streptococcus salivarius*, Microbiology, vol. 41 pp. 1451-1460 (1995).
International Search Report for PCT/AT2014/000122 dated Oct. 3, 2014.
International Search Report for PCT/AT2014/000124 dated Oct. 2, 2014.
International Search Report for PCT/AT2014/000125 dated Sep. 26, 2014.
International Search Report for PCT/AT2014/000123 dated Sep. 26, 2014.
International Preliminary Report in Patentability and Written Opinion of the International Searching Authority issued in International Application No. PCT/AT2014/00122 (10 pages).
International Preliminary Report in Patentability and Written Opinion of the International Searching Authority issued in International Application No. PCT/AT2014/00123 (8 pages).
International Preliminary Report in Patentability and Written Opinion of the International Searching Authority issued in International Application No. PCT/AT2014/00124 (8 pages).
International Preliminary Report in Patentability and Written Opinion of the International Searching Authority issued in International Application No. PCT/AT2014/00125 (8 pages).
U.S. Appl. No. 14/899,197, filed Dec. 17, 2015.
U.S. Appl. No. 14/899,212, filed Dec. 17, 2015.
U.S. Appl. No. 14/899,225, filed Dec. 17, 2015.
Singha, K., "Importance of the Phase Diagram in Lyocell Fiber Spinning", International Journal of Material's Engineering, (2012) pp. 10-16.
Schmidt, M., Lenzinger Berichte 9 (1994) pp. 95-97.
Ogawa, K., et al., "Crystal Structure of (1,3)-Alpha-D-Glucan", Water Soluble Polymers: Synthesis Solution Properties and Applications, American Chemical Society, vol. 141, (1980) p. 354.
Helfried Stover, "Zur Fasernassscheverung von Viskosefasern" Faserforschung and Textiltechnik 19, issue 10, (1968) pp. 447-452.
Rosenau et al., "The Chemistry of side reactions and byproduct formation in the system NMMO/cellulose (Lyocell process," Prog. Polym. Sci., vol. 26, pp. 1763-1837 (2001).
U.S. Appl. No. 15/932,303, filed Feb. 16, 2018.
U.S. Appl. No. 16/007,641, filed Jun. 13, 2018.
U.S. Appl. No. 15/980,140. filed May 15, 2018.
U.S. Appl. No. 15/988,401, filed May 24, 2018.
U.S. Appl. No. 16/038,471, filed Jul. 18, 2018.
U.S. Appl. No. 16/121,149, filed Sep. 4, 2018.

HIGHLY ABSORBENT POLYSACCHARIDE FIBER AND USE THEREOF

The present invention relates to a novel, highly absorbent polysaccharide fiber, its production and characteristics, and its use.

BACKGROUND OF THE INVENTION

Nonwovens are porous fabrics formed of textile fibers. Depending on the lengths of the fibers used, we distinguish between spunlaid nonwovens made of continuous fibers obtained by depositing of the fibers immediately after the spinning process, and staple nonwovens made of fibers having a defined staple length. They are produced either by a dry method, for example, by pressing of card slivers as is the case in the production of tampons, or by a wet method, e.g., similar to paper-making with subsequent solidification. Apart from natural fibers such as wool or cotton, also chemical fibers such as polypropylene or polyester are used. In the field of absorbent nonwoven products, in the overwhelming majority of cases cellulosic fibers are used because of their extremely hydrophilic nature. Their high absorption capacity builds on the ability of cellulose to form strong hydrogen bonds with water molecules. In addition, these fibers are characterized by being fully biodegradable. Apart from cotton and pulp, mainly man-made cellulose fibers, so-called regenerated cellulose fibers such as viscose or lyocell fibers, are used, as these outperform natural cellulose fibers such as cotton in terms of cleanliness, softness, and absorbent properties in many areas. For the purposes of the present invention, viscose and modal processes shall be referred to collectively as "xanthogenate processes", as in them polysaccharides are always reacted with CS2 into the respective xanthogenates. Xanthogenate processes for the production of cellulose fibers have generally been known to those skilled in the art for decades.

Examples of absorbent nonwoven products include wipes and cleaning cloths, hygiene articles such as tampons or panty liners, sterile drapes or wound treatment products for medical applications, and cosmetic products such as cleaning pads or refreshing towels. In some cases, the requirements to be fulfilled by these products vary considerably depending on their intended use. Even though there exist certain minimum requirements, especially in regard to fiber elongation and loop strength, in order to permit troublefree carding, the requirements in regard to the mechanical properties of the fibers are far lower than in the textile sector. Essential functions of absorbent nonwovens concern the absorption, the transport, the distribution, the release and/or the retention of liquids under the respective conditions of use. Numerous test methods have become established for the assessment of these properties, including water retention power to DIN 53814, immersion time, water holding capacity, absorption capacity and absorption rate according to the demand wettability test, thickness swelling and water vapor absorption. The most important requirement for the fibers used in the field of absorbent nonwovens is a high absorption capacity for water and/or liquids in general such as blood or urine. In order to quantify it, the water retention capacity and the water holding capacity are mainly used.

The water retention capacity, also referred to as swelling value, reflects the quantity of retained water following wetting and defined centrifuging relative to the dry initial weight of the fibers in percent. It is primarily determined by the supermolecular fiber structure and the pore characteristics.

The water holding capacity corresponds to the quantity of water that is retained by a wad of fibers following immersion in water and defined draining. This is mainly water retained in the capillary spaces between the fibers. Key influencing parameters pertain to the titer, the crimp, the cross-sectional shape, and the finish of the fibers.

The methods for the production of highly absorbent regenerated cellulose fibers known from literature can be divided into three groups:

1. Physical Influencing of the Fiber Structure:

The possibilities for the physical modification of the fiber structure are manifold and range from varying the composition of the spinning solution and of the spin bath to influencing the extrusion of the filament and the stretching procedure. Hollow fibers, collapsed hollow fiber structures, or fibers with multi-limbed, so-called multi-lobal cross-sections exhibit particularly high absorption capacity. Hollow fibers can, for example, be produced by adding sodium carbonate to the viscose. Upon contact with the acid spin bath, carbon dioxide is released which causes the fibers to be inflated and leads to the formation of the hollow structure. U.S. Pat. No. 4,129,679 (A) describes fibers that are produced according to such a process. A particular feature of this method is that the inflated fibers collapse upon themselves and thus form multi-limbed cross-sections. Other options that can be used to produce fibers having multi-lobal cross-sectional shapes include extruding the cellulose solution through spinnerets whose openings have three or more limbs, preferably with a length-to-width ratio of the limbs of 2:1 or more. Such a process is described in WO 8901062 (A1). Fibers having a high degree of crimp also have pronounced hydrophilic properties. It is possible, for example, to influence the crimp of viscose fibers through the use of alternative, crimp-promoting modifiers and/or low modifier concentrations that, as described in EP 0049710 (A1), may in certain circumstances be reduced down to zero, in combination with changed viscose compositions and spinning conditions.

A disadvantage of these cross-section-modified fibers is their markedly deteriorated processability in the further processing steps (e.g. carding).

2. Influencing by Incorporation of Absorbent Substances, Particularly of Polymers:

Adding hydrophilic polymers such as carboxymethylcellulose (U.S. Pat. No. 4,289,824 (A)), alginic acid or its salts (AT 402828 (B)), guar gum (WO 9855673 (A1)), or copolymers of acrylic and methacrylic acid to the cellulose solution can greatly increase the water absorption capacity of regenerated cellulose fibers. DE 2550345 (A1) describes mixed fibers of a matrix of regenerated cellulose with a high fluid holding capacity due to N-vinylamide polymer dispersed in the matrix. U.S. Pat. No. 3,844,287 (A) proposes the production of highly absorbent material of mixed fibers from a base compound of regenerated cellulose that contains evenly distributed polyacrylic acid salt. In both cases, the production of fibers takes place after the viscose process.

3. Chemical Modification of the Regenerated Cellulose Fibers or of the Employed Cellulose:

It is the aim of these methods to increase the absorption capacity by chemical reactions that are carried out directly on the regenerated cellulose fibers or on the fiber-forming cellulose. Examples include the graft copolymerization of the cellulose with acrylic acid or the carboxymethylation of viscose fibers in the low-substituted range. Such a method is disclosed, for example in JPH0351366.

From an application technology perspective, the water retention capacity is the most important parameter in the field of absorbent nonwovens, as, unlike the water holding capacity, it better replicates real-life conditions. It is not enough, for example, that a tampon or a wound dressing absorb body fluids. For it to be useful, it is essential that the absorbed fluid be retained within the fiber material, even when exposed to external forces.

The described physical fiber modifications relate substantially to surface characteristics, for example, to the cross-sectional shape and the crimp of the fibers, and thus only cause an increase of the water absorption capacity. The water retention capacity is not influenced or barely influenced.

By making chemical modifications and/or incorporating absorbent substances, the water retention capacity of the fibers can be modified, however, the introduction of non-cellulosic groups is not without problems. For example, the biodegradability may no longer be fully ensured. This is the case, for example, when copolymers of acrylic and methacrylic acid are incorporated. Another disadvantage is the danger of exceeding acceptable maximum extract or ash contents. For instance, ashing of sodium-carboxylate-group-containing cellulose fibers always leads to the formation of a certain quantity of sodium carbonate. The incorporation of charged groups renders the compliance with required pH tolerance ranges more difficult. Sodium-carboxylate-group-containing nonwovens, for example, often have a pH value that is clearly in the alkaline range.

U.S. Pat. No. 7,000,000 describes fibers obtained by spinning a solution of polysaccharides which substantially consist of repeating hexose units linked via $\alpha(1\rightarrow3)$-glycosidic bonds. These polysaccharides can be produced by bringing an aqueous solution of saccharose into contact with glucosyltransferase (GtfJ), isolated from *Streptococcus salivarius* (Simpson et al., Microbiology, vol. 41, pp 1451-1460 (1995)). As used in this context, "substantially" means that within the polysaccharide chains there may exist occasional defective locations where other bond configurations may occur. For the purposes of the present invention, these polysaccharides shall be referred to as "$\alpha(1\rightarrow3)$-glucan".

According to U.S. Pat. No. 7,000,000, the $\alpha(1\rightarrow3)$-glucan is to be derivatized, preferably acetylated. Preferably, the solvent is an organic acid, an organic halogen compound, a fluorinated alcohol, or a mixture of such components. These solvents are costly and complex to regenerate. U.S. Pat. No. 7,000,000 does not disclose any information about the absorption properties of the fibers produced in this way.

Summing up it can be stated that methods regarding the chemical modification of cellulose or regenerated cellulose fibers and the incorporation of highly absorbent substances into the cellulose matrix have not gained acceptance. The reasons for this are manifold and, for example, reside in the fact that the extra effort required by additional process steps is too high, that employed highly absorbent substances are too expensive or must be rejected from a physiological and/or toxicological viewpoint, that the desired absorption properties are not achieved, or that certain mechanical minimum standards, for example, in the case of required high degrees of filling, are not attained.

Object

In view of such prior art, the object was therefore to provide a fiber as well as a method for the production thereof, which does not require any cross-sectional or chemical modification and is entirely harmless from a physiological and/or toxicological viewpoint, however, which still exhibits a significantly increased water retention capacity.

DESCRIPTION OF THE INVENTION

The above described object is solved by a method for the production of a highly absorbent polysaccharide fiber by using a xanthogenate process, wherein the fiber-forming substance contains a mixture of cellulose and $\alpha(1\rightarrow3)$-glucan. According to the invention, this is accomplished in that an $\alpha(1\rightarrow3)$-glucan-containing sodium hydroxide solution is added to the cellulose xanthogenate solution. The addition of this glucan solution can take place at various locations of the process. For the purposes of the present invention, such a polysaccharide fiber shall also be referred to as viscose or modal fiber even though, in addition to cellulose, it also contains another fiber-forming polysaccharide, namely, said $\alpha(1\rightarrow3)$-glucan.

For the purposes of the present invention, the term "fiber" shall comprise both staple fibers having a defined staple length and continuous filaments. All principles of the invention that are described hereinafter generally apply to both staple fibers and continuous filaments.

The single fiber titer of the inventive fibers can be between 0.1 and 10 dtex. Preferably, it is between 0.5 and 6.5 dtex, and more preferably between 0.9 and 6.0 dtex. In the case of staple fibers, the staple length is usually between 0.5 and 120 mm, preferably between 20 and 70 mm, and more preferably between 35 and 60 mm. In the case of continuous filaments, the number of individual filaments in the filament yarn is between 50 and 10,000, preferably between 50 and 3,000.

The $\alpha(1\rightarrow3)$-glucan can be prepared by bringing an aqueous solution of saccharose into contact with glucosyltransferase (GtfJ) isolated from *Streptococcus salivarius* (Simpson et al., Microbiology, vol. 41, pp 1451-1460 (1995), U.S. Pat. No. 7,000,000).

In a preferred embodiment of the method according to the invention, at least 90% of the $\alpha(1\rightarrow3)$-glucan are hexose units and at least 50% of the hexose units are linked via $\alpha(1\rightarrow3)$-glycosidic bonds.

Generally, the method for the production of the inventive fiber consists of the following main steps:
1a. Preparing alkali cellulose, and its xanthogenation.
1b. Preparing an alkaline glucan solution.
2. Mixing of the two solutions.
3. Extruding the $\alpha(1\rightarrow3)$-glucan-containing spinning solution through a spinneret into a sulfuric acid spin bath, stretching the fibers, and post-treatment.

The total concentration of the fiber-forming substance in the spinning solution can be between 4 and 15% by weight, preferably it is between 5.5 and 12% by weight.

In the inventive method, the fiber-forming substance can contain between 1 and 99% by weight of $\alpha(1\rightarrow3)$-glucan. More preferably, the content of the $\alpha(1\rightarrow3)$-glucan is between 5 and 45% by weight. Below 5%, the effect of the added $\alpha(1\rightarrow3)$-glucan is too small for typical types of use of the inventive fibers; above 45%, competing reactions for the $CS_2$ in the spinning solution become too intensive, and the spinnability of the solution decreases significantly. However, under certain conditions and/or for certain types of use of the inventive fibers, both limits may be exceeded; the scope of the present invention expressly also encompasses fibers having an $\alpha(1\rightarrow3)$-glucan content between 1 and 5% by weight and between 45 and 99% by weight, respectively.

Preferably, the remaining part of the fiber-forming substance consists substantially of cellulose. As used in this context, "substantially" means that low quantities of other substances can be present which primarily originate from the cellulosic raw material, generally from said pulp. Such other substances include primarily hemicellulose and other saccharides, lignin residues, or the like. They are also contained in commercially available viscose and modal fibers.

However, the scope of the present invention shall expressly also include such fibers that, in addition to the constituents mentioned so far, also contain other polysaccharides or functional additives as generally known in the nonwoven and textile industries.

The degree of polymerization of the α(1→3) glucan employed in the method according to the invention, expressed as weight average $DP_w$, can be between 200 and 2000; values between 500 and 1000 are preferred.

A highly absorbent polysaccharide fiber produced by using a xanthogenate process and containing cellulose and α(1→3)-glucan is also the subject-matter of the present invention. The fiber-forming substance of the inventive fiber contains between 1 and 99% by weight of α(1→3)-glucan, preferably between 5 and 45% by weight of α(1→3)-glucan.

In a preferred embodiment, at least 90% of the α(1→3)-glucan of the inventive polysaccharide fiber are hexose units and at least 50% of the hexose units are linked via α(1→3)-glycosidic bonds.

Surprisingly, it was discovered that the inventive fiber has an extraordinarily high water retention capacity of at least 90%. Depending on composition and production method, the water retention capacity is even greater than 100%.

The use of the inventive fibers for the production of various dry-laid and wet-laid papers, nonwovens, hygiene articles such as tampons, panty liners, and diapers, and of other nonwovens, especially absorbent nonwoven products, but also of textile products such as yarns, woven fabrics, or knitted fabrics is also the subject-matter of the present invention.

The invention will be described below with reference to examples. However, the invention is not expressly limited to these examples but also includes all other embodiments that are based on the same inventive concept.

EXAMPLES

The degree of polymerization of the α(1→3)-glucans was determined by means of GPC in DMAc/LiCl. Subsequently, it is always the weight average of the degree of polymerization ($DP_w$) that is specified.

Example 1

An aqueous viscose xanthogenate solution containing 29.8% by weight of cellulose, 14.9% by weight of NaOH, and 8% by weight of sulfur was reacted in a dissolving unit with a first dissolving liquor containing 4.5% by weight of NaOH and then with a second dissolving liquor containing 9% by weight of α(1→3)-glucan and 4.5% by weight of NaOH, and finally with water. The viscose obtained in this way contained 8.90% by weight of fiber-forming material, 5.20% by weight of NaOH, and 2.4% by weight of sulfur (for 100% of cellulose as a fiber-forming material), with a ripeness index of 14 Hottenroth and a falling ball viscosity of 80 seconds (determined according to the Zellcheming Leaflet III/5/E). Viscose solutions with 10 and 25% of α(1→3)-glucan were prepared. The glucan quantities were related to the proportion of the α(1→3)-glucan in the fiber-forming substance. These viscose types contain 2.2% by weight of sulfur (10% of glucan and 90% of cellulose as the fiber-forming material) and 1.8% by weight of sulfur (25% of glucan and 75% of cellulose as the fiber-forming material), respectively. By using a spinneret, the solution was extruded into a regeneration bath containing 100 g/l of sulfuric acid, 330 g/l of sodium sulfate, and 15 g/l of zinc sulfate. The spinneret had 1053 perforations with a diameter of 50 μm. 0.5% by weight of a nitrogen-containing auxiliary agent were added to the viscose spinning solution. In order to achieve adequate fiber strength, stretching by approx. 75% was carried out in the secondary bath (92° C., 15 g/l of $H_2SO_4$). The draw-off velocity is 50 m/min.

In a reference example 1, the viscose from Example 1 was spun into fibers without the addition of the glucan/NaOH solution, but otherwise in the same conditions as in Example 1.

The properties of the obtained fibers are listed in Table 1.

Example 2

A viscose containing 8.70% by weight of cellulose, 5.20% by weight of NaOH, and 2.3% by weight of sulfur, with a ripeness index of 15 Hottenroth and a falling ball viscosity of 75 seconds (determined according to the Zellcheming Leaflet III/5/E) was, by means of a spinneret, extruded into a regeneration bath containing 100 g/l of sulfuric acid, 310 g/l of sodium sulfate, and 15 g/l of zinc sulfate. The spinneret had 1053 perforations with a diameter of 50 μm. 0.5% by weight of a nitrogen-containing auxiliary agent were added to the viscose spinning solution. In order to achieve adequate fiber strength, stretching by approx. 75% was carried out in the secondary bath (92° C., 15 g/l of $H_2SO_4$). The draw-off velocity is 50 m/min.

By using a positive displacement pump, suitable quantities of an aqueous α(1→3)-glucan/NaOH solution (5% by weight of NaOH, 8% by weight of α(1→3)-glucan) were added to the viscose solution upstream from the spinneret so that fibers having 10, 15, and 30% of glucan could be produced. These glucan quantities were related to the fraction of the α(1→3)-glucan in the total fiber-forming substance of the polysaccharide fibers.

In a reference example 2, the viscose from Example 2 was spun into fibers without the addition of the glucan/NaOH solution, but otherwise in the same conditions as in Example 2.

The properties of the obtained fibers are listed in Table 1.

TABLE 1

| example | additive | quantity of glucan % | titer dtex | FFk cN/tex | FDk % | WRV % |
|---|---|---|---|---|---|---|
| reference example 1 | none | — | 1.7 | 27.4 | 16.2 | 86 |
| 1a | glucan $DP_w$800 | 10 | 1.7 | 27.4 | 16.5 | 94 |
| 1b | glucan $DP_w$800 | 20 | 1.7 | 24.7 | 14.6 | 107 |
| reference example 2 | none | — | 1.3 | 29.6 | 15.8 | 87 |
| 2a | glucan $DP_w$1000 | 10 | 1.3 | 28.6 | 17.9 | 95 |

TABLE 1-continued

| example | additive | quantity of glucan % | titer dtex | FFk cN/tex | FDk % | WRV % |
|---|---|---|---|---|---|---|
| 2b | glucan $DP_w 1000$ | 15 | 1.3 | 26.1 | 18.1 | 116 |
| 2c | glucan $DP_w 1000$ | 25 | 1.3 | 23.6 | 19.4 | 124 |

FFk fiber strength, conditioned
FDk fiber elongation, conditioned
WRV water retention capacity

What is claimed is:

1. A method for the production of a highly absorbent polysaccharide fiber by a xanthogenate process comprising the steps of:
   (a) preparing an xanthogenate comprising alkali cellulose;
   (b) preparing a solution comprising α(1→3)-glucan and NaOH;
   (c) combining the xanthogenate of step (a) with the solution of step (b) to form a spinning solution, wherein a fiber forming substance in said spinning solution is a mixture of cellulose and α(1→3)-glucan; and
   (d) extruding said spinning solution to form said polysaccharide fiber.

2. The method according to claim 1, wherein the fiber-forming substance contains between 1 and 99% by weight of α(1→3)-glucan.

3. The method according to claim 2, wherein the fiber forming substance contains between 5 and 45% by weight of α(1→3)-glucan.

4. The method according to claim 1, wherein the method is a viscose process.

5. The method according to claim 1, wherein at least 90% of the α(1→3)-glucan are hexose units and at least 50% of the hexose units are linked via α(1→3)-glycosidic bonds.

6. The method according to claims 1, 2, 4, or 5, wherein the fiber is selected from the group consisting of a staple fiber and a continuous filament.

7. A highly absorbent polysaccharide fiber produced according to claim 1, wherein a fiber-forming substance of the polysaccharide fiber is a mixture of cellulose and α(1→3)-glucan.

8. A highly absorbent polysaccharide fiber comprising a fiber-forming substance, wherein the fiber forming substance is a mixture of cellulose and α(1→3)-glucan.

9. The fiber according to claim 8, wherein the fiber-forming substance contains between 1 and 99% by weight of α(1→3)-glucan.

10. The fiber according to claim 8, wherein at least 90% of the α(1→3)-glucan are hexose units and at least 50% of the hexose units are linked via α(1→3)-glucosidic bonds.

11. The fiber according to claim 8, wherein the fiber has a water retention capacity of at least 90%.

12. The fiber according to claim 7, wherein the fiber-forming substance contains between 1 and 99% by weight of α(1→3)-glucan.

13. The fiber according to claims 12 or 9, wherein the fiber forming substance contains between 5 and 45% by weight of α(1→3)-glucan.

14. The fiber according to claim 7, wherein at least 90% of the α(1→3)-glucan are hexose units and at least 50% of the hexose units are linked via α(1→3)-glycosidic bonds.

15. The fiber according to claim 7, wherein the fiber has a water retention capacity of at least 90%.

16. The fiber according to claims 15 or 11, wherein the water retention capacity is greater than 100%.

17. The fiber according to claims 7, 12, 14, 9, or 8, wherein the fiber is selected from the group consisting of a staple fiber and a continuous filament.

18. A product comprising the fiber according to claims 7 or 8, wherein the product is selected from the group consisting of nonwovens, hygiene articles, and of other, absorbent nonwoven products and papers.

19. The product according to claim 18, wherein the hygiene products are selected from the group consisting of tampons, panty liners, and diapers.

20. A textile product comprising the fiber according to claims 7 or 8, wherein the textile product is selected from the group consisting of yarns, woven fabrics, and knitted fabrics.

* * * * *

UNITED STATES PATENT AND TRADEMARK OFFICE
CERTIFICATE OF CORRECTION

PATENT NO. : 10,220,111 B2
APPLICATION NO. : 14/899214
DATED : March 5, 2019
INVENTOR(S) : Thomas Roder et al.

Page 1 of 1

It is certified that error appears in the above-identified patent and that said Letters Patent is hereby corrected as shown below:

In the Claims

Column 8, Claim 10, Line 12, "glucosidic" should read --glycosidic--.

Column 8, Claim 17, Line 27, "claims 7, 12, 14, 9, or 8" should read --claims 7, 8, 12, 14, or 15--.

Signed and Sealed this
Thirteenth Day of August, 2019

Andrei Iancu
*Director of the United States Patent and Trademark Office*